US010006031B2

(12) United States Patent
Iversen et al.

(10) Patent No.: US 10,006,031 B2
(45) Date of Patent: *Jun. 26, 2018

(54) ANTISENSE COMPOSITION AND METHOD FOR TREATING MUSCLE ATROPHY

(71) Applicant: Sarepta Therapeutics, Inc., Cambridge, MA (US)

(72) Inventors: Patrick L. Iversen, Corvallis, OR (US); Dwight D. Weller, Corvalis, OR (US); Alan P. Timmins, Sherwood, OR (US)

(73) Assignee: Sarepta Therapeutics, Inc., Cambridge, MA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/177,244

(22) Filed: Jun. 8, 2016

(65) Prior Publication Data
US 2016/0281092 A1    Sep. 29, 2016

Related U.S. Application Data

(60) Division of application No. 14/323,349, filed on Jul. 3, 2014, now abandoned, which is a continuation of application No. 12/983,798, filed on Jan. 3, 2011, now Pat. No. 8,785,410, which is a continuation of application No. 11/433,724, filed on May 11, 2006, now Pat. No. 7,888,012, which is a continuation of application No. PCT/US2006/004797, filed on Feb. 9, 2006.

(60) Provisional application No. 60/651,574, filed on Feb. 9, 2005.

(51) Int. Cl.
| A61K 31/675 | (2006.01) |
| A61K 38/00 | (2006.01) |
| A61K 47/48 | (2006.01) |
| A61K 48/00 | (2006.01) |
| C12N 15/113 | (2010.01) |
| C07H 21/00 | (2006.01) |
| C07K 7/08 | (2006.01) |
| C12Q 1/68 | (2018.01) |
| A61K 47/64 | (2017.01) |

(52) U.S. Cl.
CPC ........ *C12N 15/1136* (2013.01); *A61K 31/675* (2013.01); *A61K 47/645* (2017.08); *C07H 21/00* (2013.01); *C07K 7/08* (2013.01); *C12Q 1/6876* (2013.01); *C12N 2310/11* (2013.01); *C12N 2310/31* (2013.01); *C12N 2310/3145* (2013.01); *C12N 2310/3233* (2013.01); *C12N 2310/3513* (2013.01); *C12N 2320/30* (2013.01); *C12Q 2600/158* (2013.01); *Y10T 436/143333* (2015.01)

(58) Field of Classification Search
USPC ...... 435/6.1, 91.1, 91.31, 455, 6.12; 514/44, 514/1.1, 1.2, 81, 86; 536/23.1, 24.5; 530/327
See application file for complete search history.

(56) References Cited

U.S. PATENT DOCUMENTS

| 5,034,506 A | 7/1991 | Summerton et al. |
| 5,142,047 A | 8/1992 | Summerton et al. |
| 5,166,315 A | 11/1992 | Summerton et al. |
| 5,185,444 A | 2/1993 | Summerton |
| 5,217,866 A | 6/1993 | Summerton et al. |
| 5,506,337 A | 4/1996 | Summerton et al. |
| 5,521,063 A | 5/1996 | Summerton et al. |
| 5,627,274 A | 5/1997 | Kole et al. |
| 5,665,593 A | 9/1997 | Kole et al. |
| 5,698,685 A | 12/1997 | Summerton et al. |
| 5,916,808 A | 6/1999 | Kole et al. |
| 5,976,879 A | 11/1999 | Kole et al. |
| 6,060,456 A | 5/2000 | Arnold et al. |
| 6,103,466 A | 8/2000 | Grobet et al. |
| 6,133,246 A | 10/2000 | McKay et al. |

(Continued)

FOREIGN PATENT DOCUMENTS

| WO | WO1994246887 | 11/1994 |
| WO | WO19973461 | 9/1997 |

(Continued)

OTHER PUBLICATIONS

International Search Report & Written Opinion for Application No. PCT/US2016/056093 (dated Apr. 28, 2017).
Aartsma-Rus et al., "Theoretic Applicability of Antisense Mediated Exon Skipping for Duchenne Muscular Dystrophy Mutations," Human Mutation ; vol. 30, No. 3, pp. 293-299; p. 294, table 1, (Jan. 20, 2009).
EMBL Accession No. DQ927047, Homo sapiens isolate AFRAM_A02 myostatin (GDF8) (Dec. 15, 2016); p. 1-2; downloaded from the internet, Apr. 4, 2017.
USPTO; Restriction Requirement dated Mar. 17, 2008 in U.S. Appl. No. 11/433,724.
USPTO; Non-Final Office Action dated Sep. 17, 2008 in U.S. Appl. No. 11/433,724.

(Continued)

Primary Examiner — Jane Zara
(74) Attorney, Agent, or Firm — Snell & Wilmer LLP

(57) ABSTRACT

A method and compound for treating skeletal muscle mass deficiency in a human subject are disclosed. The composition is an oligomer of morpholino subunits and phosphorus-containing intersubunit linkages joining a morpholino nitrogen of one subunit to a 5' exocyclic carbon of an adjacent subunit, contains between 10-40 nucleotide bases, has a base sequence effective to hybridize to an expression-sensitive region of processed or preprocessed human myostatin RNA transcript, identified, in its processed form, by SEQ ID NO: 6, and is capable of uptake by target muscle cells in the subject. In practicing the method, the compound is administered in an amount and at a dosage schedule to produce an overall reduction in the level of serum myostatin measured in the patient, and preferably to bring the myostatin level within the a range determined for normal, healthy individuals.

11 Claims, 4 Drawing Sheets

(56) References Cited

U.S. PATENT DOCUMENTS

| | | |
|---|---|---|
| 6,172,216 B1 | 1/2001 | Bennnett et al. |
| 6,210,892 B1 | 4/2001 | Bennnett et al. |
| 6,214,986 B1 | 4/2001 | Bennnett et al. |
| 6,228,579 B1 | 5/2001 | Zyskind et al. |
| 6,239,265 B1 | 5/2001 | Cook |
| 6,399,312 B2 | 6/2002 | Wu-Wong et al. |
| 6,495,663 B1 | 12/2002 | Rothbard et al. |
| 6,617,440 B1 | 9/2003 | Findly |
| 6,653,467 B1 | 11/2003 | Matsuo et al. |
| 6,669,951 B2 | 12/2003 | Rothbard et al. |
| 6,677,153 B2 | 1/2004 | Iversen |
| 6,784,291 B2 | 8/2004 | Iversen et al. |
| 6,828,105 B2 | 12/2004 | Stein et al. |
| 6,841,542 B2 | 1/2005 | Bartelmez |
| 7,049,431 B2 | 5/2006 | Iversen et al. |
| 7,094,765 B1 | 8/2006 | Iversen et al. |
| 7,148,204 B2 | 12/2006 | Bennnett et al. |
| 7,468,418 B2 | 12/2008 | Iversen et al. |
| 7,534,879 B2 | 5/2009 | van Deutekom |
| 7,618,814 B2 * | 11/2009 | Bentwich ............... G06F 19/18 435/320.1 |
| 7,888,012 B2 * | 2/2011 | Iversen ................. C07H 21/00 435/455 |
| 7,977,472 B2 | 7/2011 | Beigelman et al. |
| 8,785,410 B2 * | 7/2014 | Iversen ................. C07H 21/00 435/455 |
| 9,322,019 B2 | 4/2016 | Dickson |
| 2003/0074680 A1 | 4/2003 | Lee et al. |
| 2003/0123191 A1 | 7/2003 | Kasamatsu et al. |
| 2003/0129171 A1 | 7/2003 | Grobet et al. |
| 2004/0242528 A1 | 12/2004 | Hagstrom et al. |
| 2004/0265879 A1 | 12/2004 | Iversen et al. |
| 2004/0266720 A1 | 12/2004 | Iversen et al. |
| 2005/0124566 A1 * | 6/2005 | Robin ............ C12Y 103/01022 514/44 A |
| 2006/0030522 A1 | 2/2006 | Knopf et al. |
| 2006/0276425 A1 | 12/2006 | Mourich et al. |
| 2006/0287268 A1 | 12/2006 | Iversen et al. |
| 2007/0105807 A1 | 5/2007 | Sazani et al. |
| 2007/0122821 A1 | 5/2007 | Iversen et al. |
| 2007/0249538 A1 | 10/2007 | Sazani et al. |
| 2009/0082547 A1 | 3/2009 | Iversen et al. |
| 2009/0088562 A1 | 4/2009 | Weller et al. |
| 2009/0099066 A1 | 4/2009 | Moulton et al. |
| 2009/0105139 A1 | 4/2009 | Kole et al. |
| 2009/0110689 A1 | 4/2009 | Mourich et al. |
| 2009/0246221 A1 | 10/2009 | Mourich et al. |
| 2009/0264353 A1 | 10/2009 | Orum et al. |
| 2010/0130591 A1 | 5/2010 | Sazani et al. |
| 2010/0184670 A1 | 7/2010 | Mourich et al. |
| 2013/0085139 A1 | 4/2013 | Dickson et al. |
| 2014/0045916 A1 | 2/2014 | Iversen et al. |
| 2014/0315862 A1 | 10/2014 | Kaye |
| 2015/0073140 A1 | 3/2015 | Hanson et al. |
| 2017/0022502 A1 | 1/2017 | Dickson |

FOREIGN PATENT DOCUMENTS

| | | |
|---|---|---|
| WO | WO199740854 | 11/1997 |
| WO | WO199902667 | 1/1999 |
| WO | WO200020432 | 4/2000 |
| WO | WO200172765 | 10/2001 |
| WO | WO2004097017 | 11/2004 |
| WO | WO2005107447 | 11/2005 |
| WO | WO2006000057 | 1/2006 |
| WO | WO2006086667 | 8/2006 |
| WO | WO2007058894 | 5/2007 |
| WO | WO2008051306 | 5/2008 |
| WO | WO2008131807 | 11/2008 |
| WO | WO2008153933 | 12/2008 |
| WO | WO2009086469 | 7/2009 |
| WO | WO2010048586 | 4/2010 |
| WO | WO2010080554 | 7/2010 |
| WO | WO2010129406 | 11/2010 |
| WO | WO200183740 | 11/2011 |
| WO | 2016149659 | 9/2016 |
| WO | 2017062835 | 4/2017 |

OTHER PUBLICATIONS

USPTO; Non-Final Office Action dated Jun. 11, 2009 in U.S. Appl. No. 11/433,724.
USPTO; Final Office Action dated Mar. 10, 2010 in U.S. Appl. No. 11/433,724.
USPTO;Notice of Allowance dated Sep. 29, 2010 in U.S. Appl. No. 11/433,724.
USPTO; Restriction Requirement dated Jun. 19, 2012 in U.S. Appl. No. 12/983,798.
USPTO; Non-Final Office Action dated Sep. 6, 2013 in U.S. Appl. No. 12/983,798.
USPTO; Non-Final Office Action dated Jan. 24, 2013 in U.S. Appl. No. 12/983,798.
USPTO; Notice of Allowance dated Mar. 13, 2014 in U.S. Appl. No. 12/983,798.
USPTO; Restriction Requirement dated Jun. 13, 2013 in U.S. Appl. No. 13/644,363.
USPTO; Non-Final Office Action dated Jul. 24, 2013 in U.S. Appl. No. 13/644,363.
USPTO; Non-Final Office Action dated Jan. 16, 2014 in U.S. Appl. No. 13/644,363.
USPTO; Non-Final Office Action dated Jun. 2, 2014 in U.S. Appl. No. 13/644,363.
USPTO; Restriction Requirement dated Aug. 5, 2015 in U.S. Appl. No. 14/323,349.
USPTO; Non-Final Office Action dated Dec. 10, 2015 in U.S. Appl. No. 14/323,349.
USPTO; Restriction Requirement dated Jan. 14, 2015 in U.S. Appl. No. 14/504,453.
USPTO; Non-Final Office Action dated May 27, 2015 in U.S. Appl. No. 14/504,453.
USPTO; Notice of Allowance dated Sep. 10, 2015 in U.S. Appl. No. 14/504,453.
USPTO; Notice of Allowance dated Dec. 29, 2015 in U.S. Appl. No. 14/504,453.
USPTO; Requirement for Restriction dated Nov. 17, 2016 in U.S. Appl. No. 15/078,029.
International Search Report for Application No. PCT/AU2005/000943 dated Oct. 20, 2005.
International Search Report for Application No. PCT/EP2007/061211 dated Dec. 18, 2008.
International Search Report for Application No. PCT/US1994/005181 dated Oct. 7, 1994.
International Search Report for Application No. PCT/US1999/022448 dated Dec. 23, 1999.
International Search Report for Application No. PCT/US2000/008174 dated Jul. 25, 2000.
International Search Report for Application No. PCT/US2001/014410 dated Mar. 6, 2002.
International Search Report for Application No. PCT/US2006/043651 dated Jun. 27, 2007.
International Search Report for Application No. PCT/US2007/010556 dated Mar. 13, 2008.
International Search Report for Application No. PCT/US2008/088339 dated Jun. 4, 2009.
International Search Report for Application No. PCT/US2009/061960 dated Apr. 6, 2010.
International Search Report for Application No. PCT/US2009/068599 dated May 21, 2010.
International Search Report for Application No. PCT/US2016/023239 dated Sep. 9, 2016.
CIPO; Office Action in Canadian Application No. 2,596,506 dated Apr. 5, 2016.
Invitation to Pay Additional Fees and where Applicable, Protest Fee for Application No. PCT/US2016/23239 dated Jun. 22, 2016.

(56) References Cited

OTHER PUBLICATIONS

Aartsma-Rus et al. "Antisense-mediated exon skipping: a versatile tool with therapeutic and research applications," RNA 2007, 13:1609-1624, (2007).
Agrawal et al., Site-Specific excision from RNA by Rnase H and mixed-phosphate-backbone oligodeoxynucleotides.: Proc Natl Acad Sci USA, 87(4): 1401-5, (1990).
Amali et al., "Up-Regulation of muscle-specific transcription factors during embryonic somitogenesis of zebrafish (Danio rerio) by knock-down of Myostatin-1." Developmental Dynamics 229:847-856, (2004).
Bailey, C.P., J.M. Dagle et al., "Cationic oligonucleotides can mediate specific inhibition of gene expression in Xenopus oocytes." Nucleic Acids Res, 26(21); 4860-7, (1998).
Barawkar, D.A. and T.C. Bruice, "Synthesis, biophysical properties, and nuclease resistance properties of mixed backbone oligodeoxynucleotides containing cationic internucleoside guanidinium linkages: deoxynucleic guanidine/ DNA chimeras." Proc Natl Acad Sci USA, 95 (19): 11047-52, (1998).
Bennett, M.R. and Schwartz, S.M., Circulation, 92 (7): 1981-1993, (1995).
Bestas Burcu et al., "Design and Applcation of Biospecific Splice-Switching Oligonucleotides.", Nucleic Acid Therapeutics, vol. 24, No. 1, dated Feb. 2014.
Blommers et al., Nucleic Acids Research, 22 (20): 4187-4194, (1994).
Bogdanovich et al., "Functional improvement of dystrophic muscle by myostatin blockade," Nature, 420:418-421, (2002). Abstract only.
Bonham et al., "An assesment of the antisense properties of Rnase H-competent and steric-blocking oligomers." Nucleic Acids Res 23(7): 1197-203, (1995). Abstract only.
Boudvillain et al., "Transplatin-modified oligo (2'-O-methyl ribonucleotide)s: a new tool for selective modulation of gene expression." Biochemistry, 36 (10): 2925-31, (1997). Abstract Only.
Branch et al., Trends in Biochem. Sci., 23:45-50, (1998).
Chirila et al., "The use of synthetic polymers for delivery of therapeutic antisense oligodeoxynucleotides," Biomaterials, 23: 321-342, (2002). Abstract only.
Cross et al., "Solution structure of an RNA x DNA hybrid duplex containing a 3'-thioformacetal linker and an RNA A-tract," Biochemistry, 36 (14): 4096-4107, (1997). Abstract only.
Dagle et al., "Targeted elimination of zygotic messages in Xenopus laevis embryos by modified oligonucleotides possessing terminal cationic linkages", Nucleic Acids Res., 28 (10): 2153-7, (2000).
Ding, D. et al., "An oligodeoxyribonucleotide N34 P54 phosphoramidate duplex forms an A-type helix in solution," Nucleic Acids Res., 24(2): 354-60, (1996).
Egholm et al., "PNA hybridizes to complementary oligonucleotides obeying the Watson-Crick hydrogen-bonding rules," Nature, 365 (6446): 566-568, (1993). Abstract only.
Felgner et al., "Lipofection: a highly efficient, lipid-mediated DNA-transfection procedure," PNAS, 84(21): 7413-7, (1987).
Gee, J.E., et al., "Assessment of high-affinity hybridization, RNase H cleavage, and covalent linkage in translation arrest by antisense oligonucleotides," Antisense Nucleic Acid Drug Dev., 8(2): 103-11, (1998). Abstract only.
Gonzalez-Cadavid et al., "Organization of the human myostatin gene and expression in healthy men and HIV-infected men with muscle wasting," PNAS, 95(25): 14938-14943, (1998).
Hudziak et al. "Antiproliferative effects of steric blocking phosphorodiamidate morpholino antisense agents directed against c-myc," Antisense & Nucleic Acid Drug Dev., 10(3): 163-176, (2000). Abstract only.
Hudziak et al. "Resistance of morpholino phosphorodiamidate oligomers to enzymatic degradation," Antisense & Nucleic Acid Drug Dev., 6: 267-272, (1996). Abstract only.

Jagjeet K. Kang et al.; Antisense-induced Myostatin Exon Skipping Leads to Muscle Hypertrophy in Mice Following Octa-guanidine Morpholino Oligomer Treatment; Molecular Therapy, vol. 19 No. 1, pp. 159-164, Jan. 2011.
Jen et al., "Suppression of gene expression by targeted disruption of messenger RNA: available options and current strategies," Stem Cells, 18: 307-319, (2000).
Joulia et al., "Mechanisms involved in the inhibition of myoblast proliferation and differentiation by myostatin," Experimental Cell Research, 286: 263-275, (2003).
Kirk et al., "Myostatin regulation during skeletal muscle regeneration," J. Cell Physiology, 184(3): 356-363, (2000). Abstract only.
Lappalainen et al., "Cationic liposomes improve stability and intracellular delivery of antisense oligonucleotides into CaSki cells," Biochim Biophys ACTA, 1196(2): 201-208, (1994). Abstract only.
Lesnikowski et al., "Octa(thymidine methanephosphonates) of partially defined sterochemistry: synthesis and effect of chirality at phosphorus on binding to pentadecadecadeoxyriboadenylic acid." Nucleic Acids Res., 18(8): 2109-15, (1990).
Levin et al., Position-dependent effects of locked nucleic acid (LNA) on DNA sequencing and PCR primers, Nucleic Acids Research, vol. 34, e 142, pp. 1-11, (2006).
Linkletter, B.A. and Bruice, T.C., "Solid-phase synthesis of positively charged deoxynucleic guanidine (DNG) modified oligonucleotides containing neutral urea linkages: Effect of charge deletions on binding and fidelity." Bioorg. Med. Chem. 8(11): 1893-1901, (2000).
Lou et al., "Synthetic hydrogels as carriers in antisense therapy: preliminary evaluation of an oligodeoxynucleotide covalent conjugate with a copolymer of 1-vinyl-2-pyrrolidinone and 2-hydroxyethyl methacrylate," J. Biomaterials Appl., 15(4): 307-320, (2001). Abstract only.
McPherron et al., "Regulation of skeletal muscle mass in mice by a new TGF-beta superfamily member," Nature, 387(6628): 83-90, (1997). Abstract only.
McPherron et al., "Double muscling in cattle due to mutations in the myostatin gene," PNAS, 94(23): 12457-12461, (1997).
Micklefield, J., "Backbone modification of nucleic acids: synthesis, structure and therapeutic applications." Curr Med Chem, 8(10): 1157-79 (2001).
Moulton, H. M. and J. D. Moulton, "Peptide-assisted delivery of steric-blocking antisense oligomers," Curr Opin Mol Ther., 5(2): 123-32, (2003). Abstract only.
Moulton, H.M. et al., "HIV Tat peptide enhances cellular delivery of antisense morpholino oligomers," Antisense Nucleic Acid Drug Dev., 13(1): 31-43, (2003). Abstract only.
Moulton, H.M., M.H. Nelson, et al. "Cellular uptake of antisense morpholino oligomers conjugated to arginine-rich peptides." Bioconjug Chem., 15(2): 290-9, (2004).
Palu et al., "In pursuit of new developments for gene therapy of human diseases," J. Biotech., 68: 1-13, (1999). Abstract only.
Pari, G.S., et al. "Potent antiviral activity of an antisense oligonucleotide complementary to the intron-exon boundary of human cytomegalovirus genes UL36 and UL37," Antimicrob Agents Chemother., 39(5): 1157-61, (1995).
Schulte et al., Int. J. Sport Nutrition Exercise Metab., 11 Suppl. : 111-118 (2001). Schulte et al., "Effects of resistance training on the rate of muscle protein synthesis in frail elderly people," Int. J. Sport Nutrition Exercise Metab., 11 Suppl. : 111-118, (2001). Abstract only.
Stein, D. et al., "A specificity comparison of four antisense types: morpholino, 2'-O-methyl RNA, DNA, and phosphorothioate DNA," Antisense Nucleic Acid Drug Dev., 7:(3): 151-7, (1997). Abstract only.
Summerton et al., "Morpholino and phosphorothioate antisense oligomers compared in cell-free and in-cell systems," Antisense & Nucleic Acid Drug Development, pp. 63-70, Apr. 7, 1997. Abstract only.
Summerton et al., "Morpholino antisense oligomers: the case for an RNase H-independent structural type," Biochim et. Biophys. ACTA, 1489: 141-158, (1999). Abstract only.

(56) References Cited

OTHER PUBLICATIONS

Summerton, J.J., D. Weller, "Morpholino antisense oligomers: design, preparation, and properties." Antisense Nucleic Acid Drug Dev., 7(3): 187-95, (1997). Abstract only.
Toulme, J.J., R.L. Tinevez, et al. "Targeting RNA structures by antisense oligonucleotides." Biochimie, 78(7):663-73, (1996).
Wallace et al., "Epidemiology of weight loss in humans with special reference to wasting in the elderly," Int. J. Cardiol, 85(1): 15-21, (2002). Abstract only.
Williams et al., "A single intra-articular injection of liposomally conjugated methotrexate suppresses joint inflammation in rat antigen-induced arthritis," Br. J. Rheumatology, 35(8): 719-724, (1996).
Yarasheski et al., "Serum myostatin-immunoreactive protein is increased in 60-92 year old women and men with muscle wasting," J. Nutrition, Health, Aging, 6(5): 343-348, (2002). Abstract only.
Zhu et al., "Evidence for human immunodeficiency virus type 1 replication in vivo in CD14(+) monocytes and its potential role as a source of virus in patients on highly active antiretroviral therapy," J. Virology, 76(2): 707-716, (2002).
Zimmers et al., "Induction of cachexia in mice by systemically administered myostatin," Science, 296(5572): 1486-1488, (2002). Abstract only.
Zollinger et al., "Meningococcal vaccines—present and future," Transactions of Royal Soc of Tropical Medicine and Hygiene., 85 (Supp. 1) pp. 37-43, (1991). Abstract only.
EP; Office Action dated Sep. 24, 2010 in EP Application No. 2006734779.
AU; Office Action dated Jun. 7, 2011 in AU Application No. 2006213686.
EP; Office Action dated Sep. 25, 2013 in EP Application No. 2006734779.
AU; Office Action dated Jan. 17, 2014 in AU Application No. 2003201250.
EP; Office Action dated Aug. 14, 2014 in EP Application No. 2006734779.
AU; Notice of Allowance dated Apr. 20, 2015 in AU Application No. 2003201250.
AU; Office Action dated Oct. 7, 2016 in AU Application No. 2015203791.
AU; Office Action dated Jan. 6, 2017 in AU Application No. 2015203791.
Written Opinion of the International Searching Authority for Application No. PCT/US2009/068599 dated May 21, 2010.
Written Opinion of the International Searching Authority for Application No. PCT/US2009/061960 dated Apr. 6, 2010.
Written Opinion of the International Searching Authority for Application No. PCT/US2008/088339 dated Jun. 4, 2009.
Written Opinion of the International Searching Authority for Application No. PCT/US2007/010556 dated Mar. 13, 2008.
Written Opinion of the International Searching Authority for Application No. PCT/US2006/043651 dated Jun. 27, 2007.
Written Opinion of the International Searching Authority for Application No. PCT/EP2007/0061211 dated Dec. 18, 2008.
Written Opinion of the International Searching Authority for Application No. PCT/AU2005/000943 dated Oct. 20, 2005.
PCT; International Preliminary Report on Patentability for Application No. PCT/US2006/004797 dated Feb. 9, 2006.
USPTO; Non-Final Office Action dated Jun. 15, 2017 in U.S. Appl. No. 15/078,029.
USPTO; Final Office Action dated Feb. 8, 2018 in U.S. Appl. No. 15/078,029.

* cited by examiner

ANTISENSE COMPOSITION AND METHOD FOR TREATING MUSCLE ATROPHY

CROSS REFERENCE TO RELATED APPLICATIONS

This application is a divisional of U.S. Ser. No. 14/323,349 filed on Jul. 3, 2014, now U.S. Patent Publication No. 2015/0119316 entitled "ANTISENSE COMPOSITION AND METHOD FOR TREATING MUSCLE ATROPHY." U.S. Ser. No. 14/323,349 is a continuation of U.S. Ser. No. 12/983,798 filed on Jan. 3, 2011, now U.S. Pat. No. 8,785,410 entitled "ANTISENSE COMPOSITION AND METHOD FOR TREATING MUSCLE ATROPHY." U.S. Ser. No. 12/983,798 is a continuation of U.S. Ser. No. 11/433,724 filed on May 11, 2006, now U.S. Pat. No. 7,888,012 entitled "ANTISENSE COMPOSITION AND METHOD FOR TREATING MUSCLE ATROPHY." U.S. Ser. No. 11/433,724 is a continuation-in-part of PCT Patent Application No. PCT/US06/04797 filed on Feb. 9, 2006, now WIPO Publication No. WO 2006/086667 entitled "ANTISENSE COMPOSITION AND METHOD FOR TREATING MUSCLE ATROPHY." PCT Patent Application No. PCT/US06/04797 claims priority to and the benefit of U.S. Provisional Patent Application No. 60/651,574 filed on Feb. 9, 2005 and entitled "ANTISENSE COMPOSITION AND METHOD FOR TREATING MUSCLE ATROPHY." The entire contents of all the foregoing patents and applications are incorporated herein by reference.

SEQUENCE LISTING

The Sequence Listing associated with this application is provided in text format in lieu of a paper copy, and is hereby incorporated by reference into the specification. The name of the text file containing the Sequence Listing is 67463.00837_SequenceListing.txt. The text file is about 7 KB, was created on Jun. 8, 2016, and is being submitted electronically via EFS-Web.

FIELD OF THE INVENTION

This invention relates to compounds and methods for treating muscle-wasting disease conditions, and additionally, for impacting muscle tissue development in mammalian subjects.

REFERENCES

Agrawal, S., S. H. Mayrand, et al. (1990). "Site-specific excision from RNA by RNase H and mixed-phosphate-backbone oligodeoxynucleotides." Proc Natl Acad Sci USA 87(4): 1401-5.

Bennett, M. R. and S. M. Schwartz (1995). "Antisense therapy for angioplasty restenosis. Some critical considerations." Circulation 92(7): 1981-93.

Blommers, M. J., U. Pieles, et al. (1994). "An approach to the structure determination of nucleic acid analogues hybridized to RNA. NMR studies of a duplex between 2'-OMe RNA and an oligonucleotide containing a single amide backbone modification." Nucleic Acids Res 22(20): 4187-94.

Bonham, M. A., S. Brown, et al. (1995). "An assessment of the antisense properties of RNase H-competent and steric-blocking oligomers." Nucleic Acids Res 23(7): 1197-203.

Boudvillain, M., M. Guerin, et al. (1997). "Transplatin-modified oligo(2'-O-methyl ribonucleotide)s: a new tool for selective modulation of gene expression." Biochemistry 36(10): 2925-31.

Cross, C. W., J. S. Rice, et al. (1997). "Solution structure of an RNA×DNA hybrid duplex containing a 3'-thioformacetal linker and an RNA A-tract." Biochemistry 36(14): 4096-107.

Dagle, J. M., J. L. Littig, et al. (2000). "Targeted elimination of zygotic messages in Xenopus laevis embryos by modified oligonucleotides possessing terminal cationic linkages." Nucleic Acids Res 28(10): 2153-7.

Ding, D., S. M. Grayaznov, et al. (1996). "An oligodeoxyribonucleotide N3'-->P5' phosphoramidate duplex forms an A-type helix in solution." Nucleic Acids Res 24(2): 354-60.

Egholm, M., O. Buchardt, et al. (1993). "PNA hybridizes to complementary oligonucleotides obeying the Watson-Crick hydrogen-bonding rules." Nature 365(6446): 566-8.

Felgner, P. L., T. R. Gadek, et al. (1987). "Lipofection: a highly efficient, lipid-mediated DNA-transfection procedure." Proc Natl Acad Sci USA 84(21): 7413-7.

Gait, M. J., A. S. Jones, et al. (1974). "Synthetic-analogues of polynucleotides XII. Synthesis of thymidine derivatives containing an oxyacetamido- or an oxyformamido-linkage instead of a phosphodiester group." J Chem Soc [Perkin 1] 0(14): 1684-6.

Gee, J. E., I. Robbins, et al. (1998). "Assessment of high-affinity hybridization, RNase H cleavage, and covalent linkage in translation arrest by antisense oligonucleotides." Antisense Nucleic Acid Drug Dev 8(2): 103-11.

Gonzalez-Cadavid, N. F., W. E. Taylor, et al. (1998). "Organization of the human myostatin gene and expression in healthy men and HIV-infected men with muscle wasting." PNAS 95(25): 14938-14943.

Hudziak, R. M., J. Summerton, et al. (2000). "Anti-proliferative effects of steric blocking phosphorodiamidate morpholino antisense agents directed against c-myc." Antisense Nucleic Acid Drug Dev 10(3): 163-76.

Kirk, S., et al., "Myostatin regulation during skeletal muscle regulation, J. Cell Physiology, 2000, 184(3): 356-363.

Lappalainen, K., A. Urtti, et al. (1994). "Cationic liposomes improve stability and intracellular delivery of antisense oligonucleotides into CaSki cells." Biochim Biophys Acta 1196(2): 201-8.

Lesnikowski, Z. J., M. Jaworska, et al. (1990). "Octa(thymidine methanephosphonates) of partially defined stereochemistry: synthesis and effect of chirality at phosphorus on binding to pentadecadeoxyriboadenylic acid." Nucleic Acids Res 18(8): 2109-15.

Lou, X., K. L. Garrett, et al. (2001). "Synthetic hydrogels as carriers in antisense therapy: preliminary evaluation of an oligodeoxynucleotide covalent conjugate with a copolymer of 1-vinyl-2-pyrrolidinone and 2-hydroxy-ethyl methacrylate." J Biomater Appl 15(4): 307-20.

McPherron, A. C., A. M. Lawler, et al. (1997). "Regulation of skeletal muscle mass in mice by a new TGF-beta superfamily member." Nature 387(6628): 83-90.

McPherron, A. C. and S.-J. Lee (1997). "Double muscling in cattle due to mutations in the myostatin gene." PNAS 94(23): 12457-12461.

Mertes, M. P. and E. A. Coats (1969). "Synthesis of carbonate analogs of dinucleosides. 3'-Thymidinyl 5'-thymidinyl carbonate, 3'-thymidinyl 5'-(5-fluoro-2'-deoxyuridinyl) carbonate, and 3'-(5-fluoro-2'-deoxyuridinyl) 5'-thymidinyl carbonate." J Med Chem 12(1): 154-7.

Schulte, J. N., et al. "Effects of resistance training on the rate of muscle protein synthesis in frail elderly people, Int. J. Sport Nutrition and Exercise Metab, 2001, 11 Supp, pp 111-118.

Stein, D., E., et al. (1997). "A specificity comparison of four antisense types: morpholino, 2'-O-methyl RNA, DNA, and phosphorothioate DNA." Antisense Nucleic Acid Drug Dev 7(3): 151-7.

Toulme, J. J., R. L. Tinevez, et al. (1996). "Targeting RNA structures by antisense oligonucleotides." Biochimie 78(7): 663-73.

Wallace, J. I. and R. S. Schwartz (2002). "Epidemiology of weight loss in humans with special reference to wasting in the elderly." Int J Cardiol 85(1): 15-21.

Williams, A. S., J. P. Camilleri, et al. (1996). "A single intra-articular injection of liposomally conjugated methotrexate suppresses joint inflammation in rat antigen-induced arthritis." Br J Rheumatol 35(8): 719-24.

Yarasheski, K. E., et al., Serum myostatin-immunoreactive protein is increased in 60-92 year old women and men with muscle wasting," J. Nutrition, Health, Aging, 2002, 6(5):343-348.

Zimmers, T. A., M. V. Davies, et al. (2002). "Induction of Cachexia in Mice by Systemically Administered Myostatin." Science 296(5572): 1486-1488.

BACKGROUND OF THE INVENTION

Myostatin, or growth/differentiation factor 8 (GDF-8), belongs to the transforming growth factor-β (TGF-β) superfamily (McPherron, Lawler et al. 1997). The human myostatin gene has been cloned (Gonzalez-Cadavid, Taylor et al. 1998), and it has been reported that myostatin is largely expressed in human skeletal muscle and plays an essential role in negatively regulating the growth and development of skeletal muscle (Gonzalez-Cadavid, Taylor et al. 1998).

Knock-out mice provided the first evidence that myostatin plays a key role in negatively regulating muscle development (McPherron, Lawler et al. 1997). The myostatin null mice were normal except that they were significantly larger than wild-type mice and had a large and widespread increase in skeletal muscle mass. Furthermore, it was also determined that two breeds of cattle, with the heritable characteristic of increased muscle mass, have mutations in the myostatin coding sequence (McPherron and Lee 1997). Furthermore, the serum and intramuscular concentrations of myostatin are increased in HIV-infected men with muscle wasting compared with healthy men (Gonzalez-Cadavid, Taylor et al. 1998). These data support the role of myostatin as a negative regulator of skeletal muscle growth in adult men and as a contributor to muscle wasting in HIV-infected men.

Heretofore, methods for treating muscle-wasting conditions and/or enhancing muscle mass in mammals by manipulating myostatin levels have been proposed. For example, U.S. Pat. Nos. 6,103,466 and 6,617,440, and U.S. published patent application 20030074680 A1 disclose methods for inhibiting levels of expressed myostatin by administering to a human or animal subject, an antisense compound against the myostatin transcript. To date, there is no evidence that such approaches have succeeded or would succeed as disclosed, or how one would select and monitor subjects for and during treatment. There is thus a need for a treatment method for effectively treating muscle wasting as a result of a condition such as paralysis or disease state such as, for example, aging, acquired immune deficiency syndrome, multiple sclerosis, and cancer. There is also a need for an antisense agent that can effectively accumulate in target muscle cells, e.g., with oral administration, and inhibit myostatin expression in muscle cells.

Methods for enhancing muscle mass in meat-bearing animals, by administering anti-myostatin antisense agents, have also been proposed. However, to date such approaches have not proven practical because of poor uptake of the agents and/or inability to administer the agents orally. It would thus be desirable to provide an agent that could be supplied orally, e.g., in animal feed, to enhance muscle mass in meat-bearing animals.

SUMMARY OF THE INVENTION

The invention includes, in one aspect, an antisense composition for use in increasing skeletal muscle mass in a human subject. The composition includes a substantially uncharged antisense compound (i) composed of morpholino subunits and phosphorus-containing intersubunit linkages joining a morpholino nitrogen of one subunit to a 5' exocyclic carbon of an adjacent subunit; (ii) capable of uptake by target muscle cells in the subject; (iii) containing between 10-40 nucleotide bases; and (iv) having a base sequence effective to hybridize to an expression-sensitive region of processed or preprocessed human myostatin RNA transcript, identified, in its processed form, by SEQ ID NO:6.

The morpholino subunits in the compound may be joined by phosphorodiamidate linkages, in accordance with the structure:

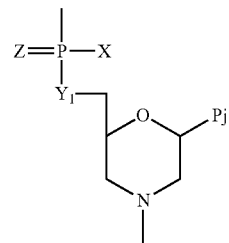

where Y1=O, Z=O, Pj is a purine or pyrimidine base-pairing moiety effective to bind, by base-specific hydrogen bonding, to a base in a polynucleotide, and X is alkyl, alkoxy, thioalkoxy, amino or alkyl amino, including dialkylamino, e.g., where X=NR2, each R is independently hydrogen or methyl. The compound may be composed of morpholino subunits linked with the uncharged linkages described above interspersed with linkages that are positively charged at physiological pH. The total number of positively charged linkages is between 2 and no more than half of the total number of linkages. The positively charged linkages have the structure above, where X is 1-piperazine.

The antisense compound in the composition may be conjugated to an arginine-rich polypeptide effective to promote uptake of the compound into target muscle cells. An exemplary arginine rich peptide has one of the sequences identified as SEQ ID NOS:7-9. The arginine-rich peptide may be covalently coupled at its C terminus to the 5' end of the antisense compound. Where the antisense compound is effective to hybridize to a target region at or adjacent the start site of the processed human myostatin transcript, the compound has a base sequence that is complementary to a target region containing at least 12 contiguous bases in a processed human myostatin transcript identified by SEQ ID NO:10, and formation of the heteroduplex in step (c) is effective to block translation of said processed transcript. An exemplary antisense sequence includes the base sequence identified by the sequence SEQ ID NO:1.

Where the antisense compound is effective to hybridize to a splice site of preprocessed human myostatin transcript, it has a base sequence that is complementary to at least 12 contiguous bases of a splice site in a preprocessed human myostatin transcript, and formation of the heteroduplex in step (c) is effective to block processing of a preprocessed myostatin transcript to produce a full-length, processed myostatin transcript. The splice site in the preprocessed myostatin transcript may have one of the sequences identified as SEQ ID NOS: 11-14. Exemplary antisense sequences are those identified by SEQ ID NOS: 2-5.

In another aspect, the invention includes a method for treating loss of skeletal muscle mass in a human subject. The steps in the method entail (a) measuring blood or tissue levels of myostatin in the subject, (b) administering to the subject, a myostatin-expression-inhibiting amount of the antisense composition described above, (c) by this administering, forming within target muscle cells in the subject, a base-paired heteroduplex structure composed of human myostatin RNA transcript and the antisense compound and having a Tm of dissociation of at least 45° C., thereby inhibiting expression of myostatin in said cells, (d) at a selected time following administering the antisense compound, measuring a blood or tissue level of myostatin in the subject, and (e) repeating the administering, using the myostatin levels measured in (d) to adjust the dose or dosing schedule of the amount of antisense compound administered, if necessary, so as to reduce measured levels of myostatin over those initially measured and maintain such levels of myostatin measured in step (d) within a range determined for normal, healthy individuals.

In one general embodiment, the myostatin value measured in step (a) is above a selected threshold for normal healthy people. The administering and measuring steps are preferably carried out over a selected period of at least 2 weeks. The administering may be by oral route.

Also forming part of the invention is a method of measuring myostatin expression levels in a mammalian subject, by (a) administering to the subject, a myostatin-expression-inhibiting amount of the substantially uncharged antisense compound of the type described above, (b) within about 8-72 hours following the administering, analyzing a body-fluid sample obtained from the subject for the presence of a heteroduplex composed of the antisense compound and a complementary region of said myostatin RNA transcript, to determine the concentration of transcript in said sample.

Also disclosed is a feed composition for a meat-producing animal, composed of a feed substance, and mixed therewith, a substantially uncharged antisense compound of the type described above.

These and other objects and features of the invention will become more fully apparent when the following detailed description is read in conjunction with the accompanying figures and examples.

DETAILED DESCRIPTION OF THE INVENTION

I. Definitions

Figure 1A:
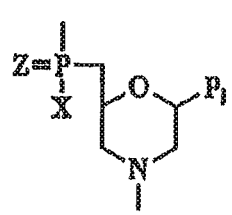
FIGS. 1A-D show several preferred morpholino-type subunits having 5-atom (FIG. 1A), six-atom (FIG. 1B) and seven-atom (FIGS. 1C and D) linking groups suitable for forming polymers.

The terms below, as used herein, have the following meanings, unless indicated otherwise.

The terms "antisense oligonucleotides," "antisense oligomer," and "antisense compound" are used interchangeably and refer to a compound having a sequence of nucleotide bases and a subunit-to-subunit backbone that allows the antisense oligomer to hybridize to a target sequence in RNA by Watson-Crick base pairing, to form an RNA:oligomer heteroduplex within the target sequence. The antisense oligonucleotide includes a sequence of purine and pyrimidine heterocyclic bases, supported by a backbone, which are effective to hydrogen-bond to corresponding, contiguous bases in a target nucleic acid sequence. The backbone is composed of subunit backbone moieties supporting the purine and pyrimidine heterocyclic bases at positions that allow such hydrogen bonding. These backbone moieties are cyclic moieties of 5 to 7 atoms in length, linked together by phosphorous-containing linkages one to three atoms long.

A substantially uncharged, phosphorus containing backbone in an oligonucleotide analog is one in which a majority of the subunit linkages, e.g., between 50-100%, are uncharged at physiological pH, and contain a single phosphorous atom. The analog contains between 12 and 40 subunits, typically about 15-25 subunits, and preferably about 18 to 25 subunits. The analog may have exact sequence complementarity to the target sequence or near complementarity, as defined below.

A "subunit" of an oligonucleotide analog refers to one nucleotide (or nucleotide analog) unit of the analog. The term may refer to the nucleotide unit with or without the attached intersubunit linkage, although, when referring to a "charged subunit", the charge typically resides within the intersubunit linkage (e.g. a phosphate or phosphorothioate linkage). A "morpholino" oligonucleotide refers to a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen with coupling through the ring nitrogen. A preferred "morpholino" oligonucleotide is composed of morpholino subunit structures of the form shown in FIG. 1A-1D, where (i) the structures are linked together by phosphorous-containing linkages, one to three atoms long, joining the morpholino nitrogen of one subunit to the 5' exocyclic carbon of an adjacent subunit, and (ii) Pi and Pj are purine or pyrimidine base-pairing moieties effective to bind, by base-specific hydrogen bonding, to a base in a polynucleotide. Exemplary structures for antisense oligonucleotides for use in the invention include the morpholino subunit types shown in FIGS. 1A-1D, with the uncharged, phosphorous-containing linkages shown in FIGS. 2A-2D. The purine or pyrimidine base-pairing moiety is typically adenine, cytosine, guanine, uracil, thymine or inosine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337, all of which are incorporated herein by reference.

A preferred morpholino oligomer is a phosphorodiamidate-linked morpholino oligomer, referred to herein as a PMO. Such oligomers are composed of morpholino subunit structures such as shown in FIG. 2B, where X=NH2, NHR, or NR2 (where R is lower alkyl, preferably methyl), Y=O, and Z=O, and Pi and Pj are purine or pyrimidine base-pairing moieties effective to bind, by base-specific hydrogen bonding, to a base in a polynucleotide, as seen in FIG. 2E. Also preferred are morpholino oligomers where the phosphordiamidate linkages are uncharged linkages as shown in FIG. 2E interspersed with cationic linkages as shown in FIG. 2F where, in FIG. 2B, X=1-piperazino. In another FIG. 2B embodiment, X=lower alkoxy, such as methoxy or ethoxy, Y=NH or NR, where R is lower alkyl, and Z=O.

As used herein, an oligonucleotide or antisense oligomer "specifically hybridizes" to a target polynucleotide if the oligomer hybridizes to the target under physiological conditions, with a thermal melting point (Tm) substantially greater than 37° C., preferably at least 45° C., and typically 50° C.-80° C. or higher. Such hybridization preferably corresponds to stringent hybridization conditions, selected to be about 10° C., and preferably about 50° C. lower than the Tm for the specific sequence at a defined ionic strength and pH. At a given ionic strength and pH, the Tm is the temperature at which 50% of a target sequence hybridizes to a complementary polynucleotide.

Polynucleotides are described as "complementary" to one another when hybridization occurs in an antiparallel configuration between two single-stranded polynucleotides. A double-stranded polynucleotide can be "complementary" to another polynucleotide, if hybridization can occur between one of the strands of the first polynucleotide and the second. Complementarity (the degree that one polynucleotide is complementary with another) is quantifiable in terms of the proportion of bases in opposing strands that are expected to form hydrogen bonds with each other, according to generally accepted base-pairing rules. An antisense compound may be complementary to a target region of a target transcript even if the two bases sequences are not 100% complementary, as long as the heteroduplex structure formed between the compound and transcript has the desired Tm stability.

As used herein the term "analog" with reference to an oligomer means a substance possessing both structural and chemical properties similar to those of the reference oligomer.

As used herein, a first sequence is an "antisense sequence" or "targeting sequence" with respect to a second sequence or "target sequence" if a polynucleotide whose sequence is the first sequence specifically binds to, or specifically hybridizes with, the second polynucleotide sequence under physiological conditions.

As used herein, "effective amount" relative to an antisense oligomer refers to the amount of antisense oligomer administered to a subject, either as a single dose or as part of a series of doses that are effective to inhibit expression of a selected target nucleic acid sequence.

As used herein, an "expression-sensitive region" of a processed or preprocessed mRNA transcript refers to either (i) a region including or adjacent the AUG start site of a processed transcript, where formation of an antisense-transcript heteroduplex is effective to inhibit translation of the transcript or (ii) a region including or adjacent a donor or acceptor splice site junction in a preprocessed transcript, where formation of an antisense-transcript heteroduplex is effective to inhibit formation of a full-length processed transcript, either because one or more exons that would normally be included in the transcript have been deleted or because the transcript has been truncated at the target splice site.

An agent is "actively taken up by mammalian cells" when the agent can enter the cell by a mechanism other than passive diffusion across the cell membrane. The agent may be transported, for example, by "active transport", referring to transport of agents across a mammalian cell membrane by e.g. an ATP-dependent transport mechanism, or by "facilitated transport", referring to transport of antisense agents across the cell membrane by a transport mechanism that requires binding of the agent to a transport protein, which then facilitates passage of the bound agent across the membrane. For both active and facilitated transport, the oligonucleotide compound has a substantially uncharged backbone, as defined below. In addition, the analog may be conjugated, e.g., at its 5' or 3' end, to an arginine rich peptide, e.g., the HIV TAT protein, or polyarginine, to facilitate transport into the target host cell, as discussed below.

As used herein, the term "myostatin antisense oligomer" refers to a nuclease-resistant phosphorus-linked morpholino antisense oligomer having high affinity for (i.e., which "specifically hybridizes to") a complementary or near-complementary human myostatin nucleic acid sequence.

As used herein "treatment" of an individual or a cell is any type of intervention used in an attempt to alter the natural course of the individual or cell. Treatment includes, but is not limited to, administration of e.g., a pharmaceutical composition, and may be performed either prophylactically, or subsequent to the initiation of a pathologic event or contact with an etiologic agent.

II. Antisense Composition for Use in Practicing the Invention Antisense Compound Antisense compounds in accordance with the present invention are substantially uncharged antisense compounds (i) composed of morpholino subunits and phosphorus-containing intersubunit linkages joining a morpholino nitrogen of one subunit to a 5' exocyclic carbon of an adjacent subunit; (ii) capable of uptake by target muscle cells in the subject; (iii) containing between 10-40 nucleotide bases; (iv) having a base sequence effective to hybridize to an expression-sensitive region of processed or preprocessed human myostatin RNA transcript, identified, in its processed form, by SEQ ID NO:6; to form a heteroduplex complex having a Tm substantially greater than 37° C., preferably at least 45° C., and (vi) nuclease resistance.

In addition, the antisense compound may have the capability for active or facilitated transport as evidenced by (i) competitive binding with a phosphorothioate antisense oligomer, and/or (ii) the ability to transport a detectable reporter into target cells.

Candidate antisense oligomers may be evaluated, according to well known methods, for acute and chronic cellular toxicity, such as the effect on protein and DNA synthesis as measured via incorporation of 3H-leucine and 3H-thymidine, respectively. In addition, various control oligonucleotides, e.g., control oligonucleotides such as sense, nonsense or scrambled antisense sequences, or sequences containing mismatched bases, in order to confirm the specificity of binding of candidate antisense oligomers. The outcome of such tests is important in discerning specific effects of antisense inhibition of gene expression from indiscriminate suppression. Accordingly, sequences may be modified as needed to limit non-specific binding of antisense oligomers to non-target nucleic acid sequences.

Heteroduplex formation. The effectiveness of a given antisense compound in forming a heteroduplex with the target mRNA may be determined by screening methods known in the art. For example, the oligomer is incubated in a cell culture containing an mRNA preferentially expressed in activated lymphocytes, and the effect on the target mRNA is evaluated by monitoring the presence or absence of (1) heteroduplex formation with the target sequence and non-target sequences using procedures known to those of skill in the art, (2) the amount of the target mRNA expressed by activated lymphocytes, as determined by standard techniques such as RT-PCR or Northern blot, (3) the amount of protein transcribed from the target mRNA, as determined by standard techniques such as ELISA or Western blotting. (See, for example, (Pari, Field et al. 1995; Anderson, Fox et al. 1996).

Uptake into cells. A second test measures cell transport, by examining the ability of the test compound to transport a labeled reporter, e.g., a fluorescence reporter, into cells, e.g., cultured myocytes. The cells are incubated in the presence of labeled test compound, added at a final concentration between about 10-300 nM. After incubation for 30-120 minutes, the cells are examined, e.g., by microscopy or FACS analysis, for intracellular label. The presence of significant intracellular label is evidence that the test compound is transported by facilitated or active transport.

In one embodiment of the invention, uptake into cells is enhanced by administering the antisense compound in combination with an arginine-rich peptide linked to the 5' or 3' end of the antisense oligomer. The peptide is typically 8-16 amino acids and consists of a mixture of arginine, and other amino acids including phenylalanine and cysteine, as discussed further below.

RNAse resistance. Two general mechanisms have been proposed to account for inhibition of expression by antisense oligonucleotides (Agrawal, Mayrand et al. 1990; Bonham, Brown et al. 1995; Boudvillain, Guerin et al. 1997). In the first, a heteroduplex formed between the oligonucleotide and the viral RNA acts as a substrate for RNaseH, leading to cleavage of the RNA. Oligonucleotides belonging, or proposed to belong, to this class include phosphorothioates, phosphotriesters, and phosphodiesters (unmodified "natural" oligonucleotides). Such compounds expose the RNA in an oligomer:RNA duplex structure to hydrolysis by RNaseH, and therefore loss of function.

A second class of oligonucleotide analogs, termed "steric blockers" or, alternatively, "RNaseH inactive" or "RNaseH resistant", have not been observed to act as a substrate for RNaseH, and act by sterically blocking target RNA nucleo-cytoplasmic transport, splicing, translation, or replication. This class includes methylphosphonates (Toulme, Tinevez et al. 1996), morpholino oligonucleotides, peptide nucleic acids (PNA's), certain 2'-O-allyl or 2'-O-alkyl modified oligonucleotides (Bonham, Brown et al. 1995), and N3'→P5' phosphoramidates (Ding, Grayaznov et al. 1996; Gee, Robbins et al. 1998).

A test oligomer can be assayed for its RNaseH resistance by forming an RNA:oligomer duplex with the test compound, then incubating the duplex with RNaseH under a standard assay conditions, as described (Stein, Foster et al. 1997). After exposure to RNaseH, the presence or absence of intact duplex can be monitored by gel electrophoresis or mass spectrometry.

In vivo uptake. In accordance with another aspect of the invention, there is provided a simple, rapid test for confirming that a given antisense oligomer type provides the required characteristics noted above, namely, high Tm, ability to be actively taken up by the host cells, and substantial resistance to RNaseH. This method is based on the discovery that a properly designed antisense compound will form a stable heteroduplex with the complementary portion of the RNA target when administered to a mammalian subject, and the heteroduplex subsequently appears in the urine (or other body fluid). Details of this method are also given in co-owned U.S. Pat. No. 6,365,351 for "Non-Invasive Method for Detecting Target RNA," the disclosure of which is incorporated herein by reference.

Briefly, a test morpholino oligomer having an uncharged phosphorus-containing backbone to be evaluated, and having a base sequence targeted against a known myostatin RNA sequence (not necessarily an expression-sensitive region of the RNA transcript), is injected into a mammalian subject. Several hours (typically 8-72) after administration, the urine is assayed for the presence of the antisense-RNA heteroduplex. If heteroduplex is detected, the backbone is suitable for use in the antisense oligomers of the present invention.

The test oligomer may be labeled, e.g. by a fluorescent or a radioactive tag, to facilitate subsequent analyses, if it is appropriate for the mammalian subject. The assay can be in any suitable solid-phase or fluid format. Generally, a solid-phase assay involves first binding the heteroduplex analyte to a solid-phase support, e.g., particles or a polymer or test-strip substrate, and detecting the presence/amount of heteroduplex bound. In a fluid-phase assay, the analyte sample is typically pretreated to remove interfering sample components. If the oligomer is labeled, the presence of the heteroduplex is confirmed by detecting the label tags. For non-labeled compounds, the heteroduplex may be detected by immunoassay if in solid phase format or by mass spectroscopy or other known methods if in solution or suspension format.

Structural features. As detailed above, the antisense oligomer has a base sequence directed to a targeted portion of a cellular gene, preferably the region at or adjacent the start codon or a processed transcript or a region at or adjacent a splice site junction of the myostatin mRNA or preprocessed transcript. In addition, the oligomer is able to effectively inhibit expression of the targeted gene when administered to a host cell, e.g. in a mammalian subject. This requirement is met when the oligomer compound (a) has the ability to be taken up by muscle cells, and (b) once taken up, form a duplex with the target RNA with a Tm greater than about 45° C., preferably greater than 50° C.

The ability to be taken up selectively by activated immune cells requires, in part, that the oligomer backbone be substantially uncharged. The ability of the oligomer to form a stable duplex with the target RNA will depend on the oligomer backbone, the length and degree of complementarity of the antisense oligomer with respect to the target, the ratio of G:C to A:T base matches, and the positions of any mismatched bases. The ability of the antisense oligomer to resist cellular nucleases promotes survival and ultimate delivery of the agent to the cell cytoplasm.

Antisense oligonucleotides of 15-20 bases are generally long enough to have one complementary sequence in the mammalian genome. In addition, antisense compounds having a length of at least 12, typically at least 15 nucleotides in length hybridize well with their target mRNA. Due to their hydrophobicity, antisense oligonucleotides tend to interact well with phospholipid membranes, and it has been suggested that following the interaction with the cellular plasma membrane, oligonucleotides are actively transported into living cells (Loke, Stein et al. 1989; Yakubov, Deeva et al. 1989; Anderson, Xiong et al. 1999).

Morpholino oligonucleotides, particularly phosphoramidate- or phosphorodiamidate-linked morpholino oligonucleotides have been shown to have high binding affinities for complementary or near-complementary nucleic acids. Morpholino oligomers also exhibit little or no non-specific antisense activity, afford good water solubility, are immune to nucleases, and are designed to have low production costs (Summerton and Weller 1997).

Morpholino oligonucleotides (including antisense oligomers) are detailed, for example, in co-owned U.S. Pat. Nos. 5,698,685, 5,217,866, 5,142,047, 5,034,506, 5,166, 315, 5,185,444, 5,521,063, and 5,506,337, all of which are expressly incorporated by reference herein As noted above, the antisense oligomers for use in practicing the invention are composed of morpholino subunits of the form shown in the above cited patents, where (i) the morpholino groups are linked together by uncharged phosphorus-containing linkages, one to three atoms long, joining the morpholino nitrogen of one subunit to the 5' exocyclic carbon of an adjacent subunit, and (ii) the base attached to the morpholino group is a purine or pyrimidine base-pairing moiety effective to bind, by base-specific hydrogen bonding, to a base in a polynucleotide. The purine or pyrimidine base-pairing moiety is typically adenine, cytosine, guanine, uracil or thymine. Preparation of such oligomers is described in detail in U.S. Pat. No. 5,185,444 (Summerton et al., 1993), which is hereby incorporated by reference in its entirety. As shown in this reference, several types of non-ionic linkages may be used to construct a morpholino backbone.

Exemplary subunit structures for antisense oligonucleotides of the invention include the morpholino subunit types shown in FIGS. 1A-D, each linked by an uncharged, phosphorous-containing subunit linkage, as shown in FIGS. 2A-2D, respectively. In these figures, the X moiety pendant from the phosphorous may be any of the following: fluorine; an alkyl or substituted alkyl; an alkoxy or substituted alkoxy; a thioalkoxy or substituted thioalkoxy; or, an unsubstituted, monosubstituted, or disubstituted nitrogen, including cyclic structures. Alkyl, alkoxy and thioalkoxy preferably include 1-6 carbon atoms, and more preferably 1-4 carbon atoms. Monosubstituted or disubstituted nitrogen preferably refers to lower alkyl substitution, and the cyclic structures are preferably 5- to 7-membered nitrogen heterocycles optionally containing 1-2 additional heteroatoms selected from oxygen, nitrogen, and sulfur. Z is sulfur or oxygen, and is preferably oxygen.

Figure 1B:
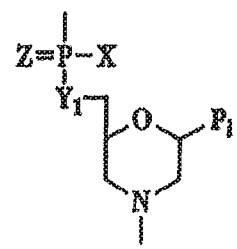
Figure 2A:
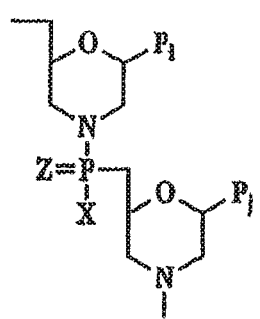
FIGS. 2A-D show the repeating subunit segment of exemplary uncharged, morpholino oligonucleotides having phosphorus-containing linkages, designated FIG. 2A through 2D, constructed using subunits A-D, respectively, of FIG. 1.
Figure 2B:
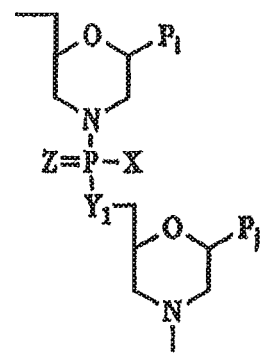

FIG. 1A shows a phosphorous-containing linkage which forms the five atom repeating-unit backbone shown in FIG. 2A, where the morpholino rings are linked by a 1-atom phosphoamide linkage. Subunit B in FIG. 1B is designed for 6-atom repeating-unit backbones, as shown in FIG. 2B. In FIG. 1B, the atom Y linking the 5' morpholino carbon to the phosphorous group may be sulfur, nitrogen, carbon or, preferably, oxygen. The X moiety pendant from the phosphorous may be any of the following: fluorine; an alkyl or substituted alkyl; an alkoxy or substituted alkoxy; a thioalkoxy or substituted thioalkoxy; or, an unsubstituted, monosubstituted, or disubstituted nitrogen, including cyclic structures. Z is sulfur or oxygen, and is preferably oxygen. Particularly preferred morpholino oligonucleotides include those composed of morpholino subunit structures of the form shown in FIG. 2B, where X is an amine or alkyl amine of the form X=NR2, where R is independently H or CH3, that is where X=NH2, X=NHCH3 or X=N(CH3)2, Y=O, and Z=O.

Figure 1C:
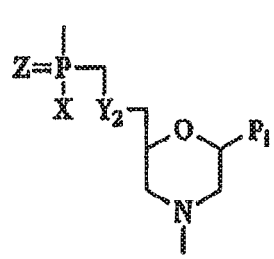
Figure 1D:
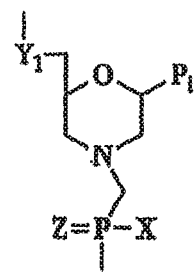
Figure 2C:
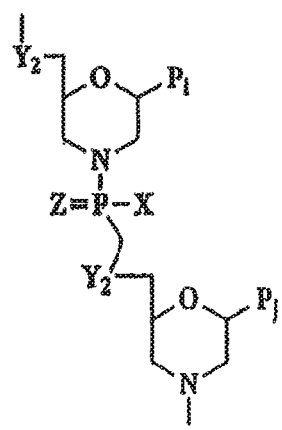
Figure 2D:
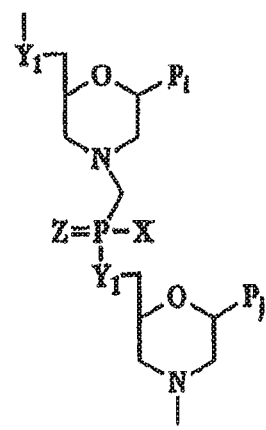
Figure 2E:
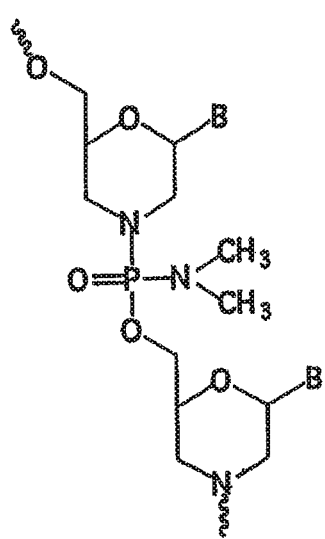
FIG. 2E is another example of an uncharged linkage type in an oligonucleotide analog.
Figure 2F:
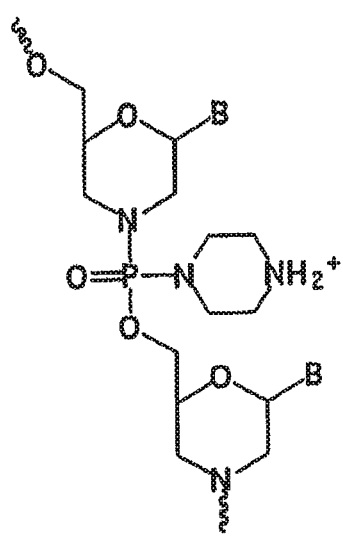
FIG. 2F is an example of a preferred charged, cationic linkage.

Subunits C-D in FIGS. 1C-D are designed for 7-atom unit-length backbones as shown for structures in FIGS. 2C and D. In Structure C, the X moiety is as in Structure B, and the moiety Y may be methylene, sulfur, or preferably oxygen. In Structure D, the X and Y moieties are as in Structure B. In all subunits depicted in FIGS. 1 and 2, each Pi and Pj is a purine or pyrimidine base-pairing moiety effective to bind, by base-specific hydrogen bonding, to a base in a polynucleotide, and is preferably selected from adenine, cytosine, guanine and uracil.

As noted above, the substantially uncharged oligomer may advantageously include a limited number of charged linkages, e.g. up to about 1 per every 5 uncharged linkages. In the case of the morpholino oligomers, such a charged linkage may be a linkage as represented by any of FIGS. 2A-D, preferably FIG. 2B, where X is oxide (—O—) or sulfide (—S—).

Also shown is a cationic linkage in FIG. 2F wherein the nitrogen pendant to the phosphate atom in the linkage of FIG. 2E is replaced with a 1-piperazino structure. The method for synthesizing the 1-piperazino group linkages is described below with respect to FIG. 3.

Preferred Antisense Targets. In the method and composition of the invention, the antisense oligomer is designed to hybridize to an expression-sensitive region of the myostatin nucleic acid sequence, under physiological conditions with a Tm substantially greater than 37° C., e.g., at least 50° C. and preferably 60° C. to 80° C. The antisense compound is designed to have high-binding affinity to the nucleic acid and may be 100% complementary to the myostatin target sequence or may include mismatches, e.g., to accommodate allelic variants, as long as the heteroduplex formed between the oligomer and myostatin target sequence is sufficiently stable to withstand the action of cellular nucleases and other modes of degradation during its transit from cell to body fluid. Mismatches, if present, are less destabilizing toward the end regions of the hybrid duplex than in the middle. The number of mismatches allowed will depend on the length of the oligomer, the percentage of G:C base pair in the duplex and the position of the mismatch(es) in the duplex, according to well understood principles of duplex stability.

Although such an antisense oligomer is not necessarily 100% complementary to the myostatin target sequence, it is effective to stably and specifically bind to the target sequence such that expression of myostatin is modulated. The appropriate length of the oligomer to allow stable, effective binding combined with good specificity is about 8-40 nucleotide base units, and preferably about 12-25 nucleotides. Oligomer bases that allow degenerate base pairing with target bases are also contemplated, assuming base-pair specificity with the target is maintained.

In one preferred approach, the target for modulation of gene expression using the antisense methods of the present invention comprises a sequence spanning or adjacent to the mRNA translational start codon for myostatin. In an alternative preferred approach, a splice acceptor or donor region of preprocessed myostatin mRNA is targeted. It will be understood that other regions of myostatin mRNA may be targeted, including one or more of, an initiator or promoter site, an intron or exon junction site, a 3'-untranslated region, and a 5'-untranslated region. It will be further understood that both spliced and unspliced RNA may serve as the template for design of antisense oligomers for use in the methods of the invention (See, e.g., Hudziak, Summerton et al. 2000).

Table 1 below lists exemplary target regions in the human myostatin gene (SEQ ID NOS:10-14). The translational start site target (MSTN-AUG) covers a region from −28 to +24 relative to the A residue of the ATG start codon (shown in bold). The Nucleotide Region (Nct. Region) is relative to a human bacterial artificial chromosome sequence (GenBank Accession No. AC073120) that contains the myostatin gene. For the splice donor (SD) and splice acceptor (SA) targets the splice site is indicated within the sequence with "|". The specific target regions for the antisense oligomers listed in Table 2 are contained within the target sequences shown in Table 1 and are exemplary. It is fully anticipated that alternative antisense oligomers that target different sequences within those shown in Table 1 would function to effectively decrease the expression of the myostatin gene.

TABLE 1

Human Myostatin Target Regions

| Name | Target Sequence (5' to 3') | Nct. Region (AC073120) | SEQ ID NO |
|---|---|---|---|
| MSTN-AUG | GAAAAAGATTATATTGATTTTAAAATCATGCAAAAACTGCAACTCTGTGTT | 29692-29743 | 10 |
| MSTN-SD1 | ACAATCATTACCATGCCTACAGAGT/GTAAGTAGTCCTATTAGTGTATATC | 29318-29367 | 11 |
| MSTN-SA2 | CTTTTCTTTTCTTATTCATTTATAG/CTGATTTTCTAATGCAAGTGGATGG | 27530-27579 | 12 |
| MSTN-SD2 | CCCAGGACCAGGAGAAGATGGGCTG/GTAAGTGATAACTGAAAATAACATT | 27156-27205 | 13 |
| MSTN-SA3 | TGATTGTTCTTTCCTTTTCAAACAG/AATCCGTTTTTAGAGGTCAAGGTAA | 24733-24782 | 14 |

Exemplary antisense oligomers to myostatin and their targets are provided in Table 2, below. The complement to the myostatin translational start codon is indicated in bold.

TABLE 2

Exemplary Myostatin Antisense Oligomers

| Name | Antisense Oligomer (5' to 3') Targeting Sequence | Target Ncts. | GenBank Acc. # | SEQ ID NO. |
|---|---|---|---|---|
| MSTN-AUG | GAGTTGCAGTTTTTGCATG | 133-151 | AF104922 | 1 |
| MSTN-SD1 | ACTCTGTAGGCATGGTAATG | 487-506 | AF104922 | 2 |
| MSTN-SD2 | CAGCCCATCTTCTCCTGG | 730-747 | AF104922 | 3 |
| MSTN-SA2 | CACTTGCATTAGAAAATCAG | 507-526 | AF104922 | 4 |
| MSTN-SA3 | CTTGACCTCTAAAAACGGATT | 881-901 | AF104922 | 5 |

In exemplary embodiments of the invention, the antisense oligomer is a PMO containing the sequences presented as SEQ ID NOS:1-5.

Oligomers as long as 40 bases may be suitable, where at least a minimum number of bases, e.g., 12 bases, are complementary to the target sequence. In general, however, facilitated or active uptake in cells is optimized at oligomer lengths less than about 30, preferably less than 25. For PMO oligomers, described further below, an optimum balance of binding stability and uptake generally occurs at lengths of 15-22 bases. The effectiveness of a given antisense oligomer molecule in forming a heteroduplex with the target RNA may be determined by screening methods known in the art. For example, the oligomer is incubated a cell culture expressing myostatin and the effect on the target RNA is evaluated by monitoring the presence or absence of (1) heteroduplex formation with the target sequence and non-target sequences using procedures known to those of skill in the art, (2) the amount of myostatin mRNA, as determined by standard techniques such as RT-PCR or Northern blot, or (3) the amount of myostatin protein, as determined by standard techniques such as ELISA or immunoblot (e.g. Western blot).

The antisense activity of the oligomer may be enhanced by using a mixture of uncharged and cationic phosphorodiamidate linkages as shown in FIGS. 2G and 2F. The total number of cationic linkages in the oligomer can vary from 1 to 10, and be interspersed throughout the oligomer. Preferably the number of charged linkages is at least 2 and no more than half the total backbone linkages, e.g., between 2-8 positively charged linkages, and preferably each charged linkages is separated along the backbone by at least one, preferably at least two uncharged linkages. The antisense activity of various oligomers can be measured in vitro by fusing the oligomer target region to the 5' end a reporter gene (e.g. firefly luciferase) and then measuring the inhibition of translation of the fusion gene mRNA transcripts in cell free translation assays. The inhibitory properties of oligomers containing a mixture of uncharged and cationic linkages can be enhanced between, approximately, five to 100 fold in cell free translation assays.

III. Treatment of Muscle Wasting

The invention provides methods for treatment of muscle wasting with an antisense oligonucleotide directed against a nucleic acid sequence encoding myostatin, and is based on the discovery that a stable, substantially uncharged phosphorus-linked morpholino antisense compound, characterized by high Tm, capable of active or facilitated transport into cells, and capable of binding with high affinity to a complementary or near-complementary myostatin nucleic acid sequence, can be administered to a human subject or patient and inhibit expression of myostatin by muscle cells resulting in increased of muscle growth.

In vivo administration of a myostatin antisense oligomer to a subject using the methods described herein can result in an improved muscle mass for the patient, with the extent improvement dependent upon dose and frequency of myostatin antisense oligomer administration and the general condition of the subject.

In preferred applications of the method the subject is a human patient diagnosed as having degenerated or reduced muscle mass secondary to a primary indication or disease state such as cancer, acquired immune deficiency syndrome (AIDS) or muscular dystrophy. The patient may also be one who does not have a muscle wasting disease but be in need of maintaining or increasing muscle mass and tone to offset normal loss of muscle mass as one ages, or muscle loss due to an extended period of inactivity.

As a first step in the treatment method, the patient is tested for myostatin levels, typically using a standard assay for measuring serum myostatin levels. See, for example, Yarasheski, et al., Schulte et al., and Kirk, et al. for methods and reagents for measuring serum myostatin-immunoreactive levels. If the measured levels are above a selected threshold level for normal average individuals, and typically more than 10-20% above the selected threshold, or if the patient otherwise presents with obvious muscle wasting, the patient is a candidate for the treatment method. Normal threshold values may be determined for normal healthy individuals within a certain gender and/or age bracket, e.g., men in the 20-35 years old age group, but more typically, values for normal patients in the same category as the test patients are preferred, except for very elderly patients, e.g., above age 70. Alternatively, levels of myostatin transcript may be determined using the heteroduplex detection method described below.

In another embodiment, the treatment is applied to patients who are likely candidates for loss of muscle, e.g., those who are subject to extended periods of inactivity, even though measured levels of myostatin may be within a normal range.

Treatment Regimens

After identifying the patient as a treatment candidate, the patient is administered an amount of the antisense compound effective to raise measured myostatin levels over a suitable response period, e.g., 1-3 days following administration of the antisense compound.

In accordance with the invention, effective delivery of an oligomer antisense to a human subject may include, but is not limited to, various systemic routes, including oral and parenteral routes, e.g., intravenous (IV), subcutaneous, intraperitoneal (IP), and intramuscular; as well as inhalation and transdermal delivery. It is appreciated that any methods effective to deliver a myostatin antisense oligomer to into the bloodstream of a subject are also contemplated. Transdermal delivery of antisense oligomers may be accomplished by use of a pharmaceutically acceptable carrier adapted for e.g., topical administration. One example of morpholino oligomer delivery is described in PCT patent application WO 97/40854, incorporated herein by reference.

In one preferred embodiment, the oligomer is a phosphorodiamidate morpholino oligomer (PMO), contained in a pharmaceutically acceptable carrier, and delivered orally. In a further aspect of this embodiment, a morpholino myostatin antisense oligonucleotide is administered at regular intervals for a short time period, e.g., daily for two weeks or less. However, in some cases the antisense oligomer is administered intermittently over a longer period of time.

Typically, one or more doses of antisense oligomer are administered, generally at regular intervals for a period of about one to two weeks. Preferred doses for oral administration are from about 1 mg oligomer/patient to about 100 mg oligomer/patient (based on an adult weight of 70 kg). In some cases, doses of greater than 100 mg oligomer/patient may be necessary. For IV administration, the preferred doses are from about 0.5 mg oligomer/patient to about 10 mg oligomer/patient (based on an adult weight of 70 kg). The antisense compound is generally administered in an amount sufficient to result in a peak blood concentration of at least 200-400 nM antisense oligomer. Greater or lesser amounts of oligonucleotide may be administered as required and maintenance doses may be lower.

At regular intervals during the treatment method, e.g., 1-3 days following administration of the antisense compound, the patient is monitored for changes in myostatin levels, e.g., serum myostatin-immunoreactive protein. The dose of antisense compound administered to the patient should be such as to reduce measured myostatin level over the initially measured level. Typically a decrease in measured myostatin level of at least 10-20% over initial levels is desired. If the initial measured levels were above a selected threshold for normal healthy individuals, the dose of antisense compound is preferably adjusted to bring the myostatin level within this normal range, and the treatment is continued, as needed to maintain myostatin levels within this range. Diagnosis and monitoring of muscle wasting generally involves monitoring weight loss due to increased skeletal muscle breakdown (Wallace and Schwartz 2002). Such methods may be qualitative or quantitative.

In some cases, the treatment regimen will include further intervention such as radiation therapy, immunotherapy and/or additional chemotherapy. Such treatment may occur prior to, during or subsequent to administration of the chemotherapeutic agent and myostatin antisense oligomer.

Materials and Methods

Phosphorodiamidate Morpholino Oligomers

PMO were synthesized and purified at AVI BioPharma, Inc. (Corvallis, Oreg.) as previously described (Geller, Deere et al. 2003, Summerton and Weller, 1997), dissolved in water, filtered through a 0.2 µM membrane (HT Tuffryn™, Gelman Sciences, Inc., Ann Arbor, Mich.), and stored at 4° C. Exemplary sequences of PMO used are shown in Table 2. The concentration of PMO was determined spectrophotometrically by measuring the absorbance at 260 nm and calculating the molarity using the appropriate extinction coefficient.

Figure 3:
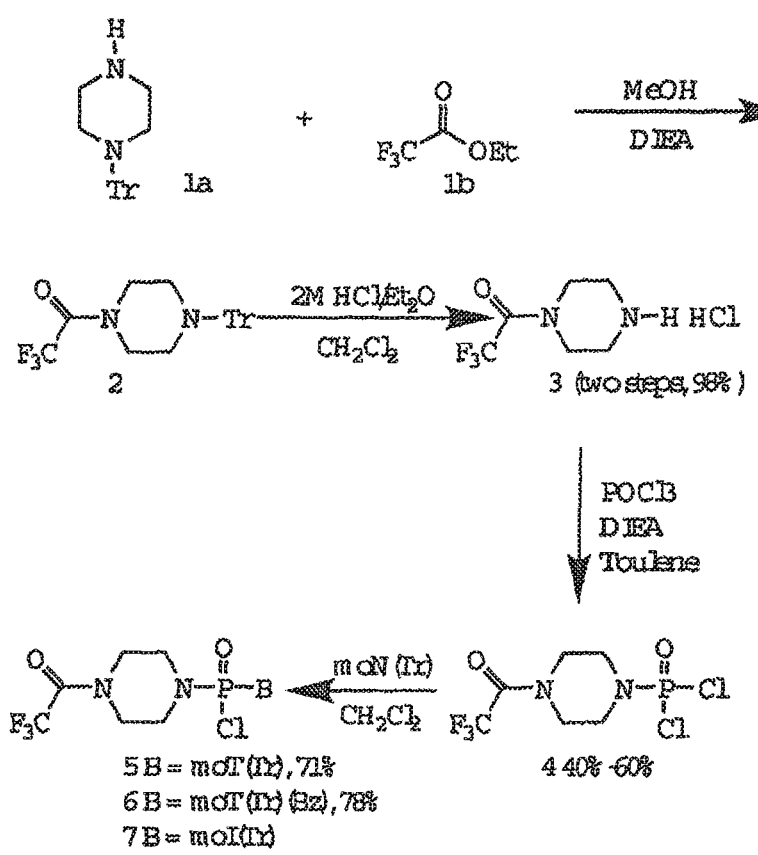
FIG. 3 shows the synthetic steps to produce subunits used to produce +PMO containing the (1-piperazino) phosphinylideneoxy cationic linkage as shown in FIG. 2F.

A schematic of a synthetic pathway that can be used to make morpholino subunits containing a (1 piperazino) phosphinylideneoxy linkage is shown in FIG. 3; further experimental detail for a representative synthesis is provided in Materials and Methods, below. As shown in the Figure, reaction of piperazine and trityl chloride gave trityl piperazine (1a), which was isolated as the succinate salt. Reaction with ethyl trifluoroacetate (1b) in the presence of a weak base (such as diisopropylethylamine or DIEA) provided 1-trifluoroacetyl-4-trityl piperazine (2), which was immediately reacted with HCl to provide the salt (3) in good yield. Introduction of the dichlorophosphoryl moiety was performed with phosphorus oxychloride in toluene.

The acid chloride (4) is reacted with morpholino subunits (moN), which may be prepared as described in U.S. Pat. No. 5,185,444 or in Summerton and Weller, 1997 (cited above), to provide the activated subunits (5,6,7). Suitable protecting groups are used for the nucleoside bases, where necessary; for example, benzoyl for adenine and cytosine, isobutyryl for guanine, and pivaloylmethyl for inosine. The subunits containing the (1 piperazino) phosphinylideneoxy linkage can be incorporated into the existing PMO synthesis protocol, as described, for example in Summerton and Weller (1997), without modification.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

Although the invention has been described with reference to particular embodiments and applications, it will be appreciated that various changes and modifications may be made without departing from the invention.

It is claimed:

1. An antisense morpholino oligonucleotide of 15-40 bases, comprising a base sequence that is complementary to at least 12 contiguous bases of SEQ ID NO: 6, wherein the antisense morpholino oligonucleotide inhibits the expression of human myostatin in a cell, and wherein the antisense morpholino oligonucleotide comprises phosphorus-containing intersubunit linkages, in accordance with the structure:

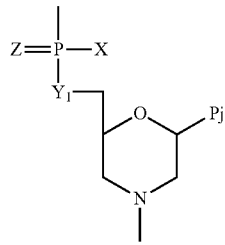

wherein each intersubunit linkage is independently selected from the group where $Y_1$ is O, Z is O, Pj is a purine or pyrimidine base-pairing moiety effective to bind, by base-specific hydrogen bonding, to a base in a polynucleotide, and X is alkyl, alkoxy, thioalkoxy, amino, alkyl amino, dialkylamino, or 1-piperazine.

2. The antisense morpholino oligonucleotide of claim 1, wherein the antisense morpholino oligonucleotide is conjugated to an arginine-rich peptide.

3. The antisense morpholino oligonucleotide of claim 1, wherein at least 2 and no more than half of the total number of phosphorus-containing intersubunit linkages are positively charged at physiological pH.

4. The antisense morpholino oligonucleotide of claim 3, wherein
   X, for any uncharged linkages, is independently alkyl, alkoxy, thioalkoxy, or an alkyl amino of the form $NR_2$, where each R is independently hydrogen or methyl, and X, for any positively charged linkages, is 1-piperazine.

5. The antisense morpholino oligonucleotide of claim 2, wherein the arginine rich peptide is selected from SEQ ID NOS: 7-9.

6. The antisense morpholino oligonucleotide of claim 2, wherein the arginine-rich peptide is covalently coupled at its C terminus to the 5' end of the antisense morpholino oligonucleotide.

7. The antisense morpholino oligonucleotide of claim 1, wherein the base sequence is complementary to at least 12 contiguous bases of SEQ ID NO: 10.

8. The antisense morpholino oligonucleotide of claim 7, wherein the base sequence is SEQ ID NO: 1.

9. The antisense morpholino oligonucleotide of claim 1, wherein the base sequence is complementary to at least 12 contiguous bases of a splice site in a preprocessed human myostatin transcript.

10. The antisense morpholino oligonucleotide of claim 9, wherein the splice site in the preprocessed myostatin transcript has a sequence selected from SEQ ID NOS: 11-14.

11. The antisense morpholino oligonucleotide of claim 10, wherein the base sequence is selected from SEQ ID NOS: 2-5.

* * * * *

SEQUENCE LISTING

<160> NUMBER OF SEQ ID NOS: 14

<210> SEQ ID NO 1
<211> LENGTH: 19
<212> TYPE: DNA
<213> ORGANISM: Artificial Sequence
<220> FEATURE:
<223> OTHER INFORMATION: synthetic antisense oligomer

<400> SEQUENCE: 1
gagttgcagt ttttgcatg                                              19

<210> SEQ ID NO 2
<211> LENGTH: 20
<212> TYPE: DNA
<213> ORGANISM: Artificial Sequence
<220> FEATURE:
<223> OTHER INFORMATION: synthetic antisense oligomer

<400> SEQUENCE: 2
actctgtagg catggtaatg                                             20

<210> SEQ ID NO 3
<211> LENGTH: 18
<212> TYPE: DNA
<213> ORGANISM: Artificial Sequence
<220> FEATURE:
<223> OTHER INFORMATION: synthetic antisense oligomer

<400> SEQUENCE: 3
cagcccatct tctcctgg                                               18

<210> SEQ ID NO 4
<211> LENGTH: 20
<212> TYPE: DNA
<213> ORGANISM: Artificial Sequence
<220> FEATURE:
<223> OTHER INFORMATION: synthetic antisense oligomer

<400> SEQUENCE: 4
cacttgcatt agaaaatcag                                             20

<210> SEQ ID NO 5
<211> LENGTH: 21
<212> TYPE: DNA
<213> ORGANISM: Artificial Sequence
<220> FEATURE:
<223> OTHER INFORMATION: synthetic antisense oligomer

<400> SEQUENCE: 5
cttgacctct aaaaacggat t                                           21

<210> SEQ ID NO 6
<211> LENGTH: 2823
<212> TYPE: DNA
<213> ORGANISM: Homo sapiens

<400> SEQUENCE: 6
agattcactg gtgtggcaag ttgtctctca gactgtacat gcattaaaat tttgcttggc    60
attactcaaa agcaaagaa aagtaaaagg aagaaacaag aacaagaaaa aagattatat   120
tgattttaaa atcatgcaaa aactgcaact ctgtgtttat atttacctgt ttatgctgat   180
tgttgctggt ccagtggatc taaatgagaa cagtgagcaa aaagaaaatg tggaaaaaga   240
ggggctgtgt aatgcatgta cttggagaca aaacactaaa tcttcaagaa tagaagccat   300

```
taagatacaa atcctcagta aacttcgtct ggaaacagct cctaacatca gcaaagatgt      360
tataagacaa cttttaccca aagctcctcc actccgggaa ctgattgatc agtatgatgt      420
ccagagggat gacagcagcg atggctcttt ggaagatgac gattatcacg ctacaacgga      480
aacaatcatt accatgccta cagagtctga ttttctaatg caagtggatg aaaacccaa       540 atgttgcttc tttaaattta gctctaaaat acaatacaat aaagtagtaa aggcccaact      600
atggatatat ttgagacccg tcgagactcc tacaacagtg tttgtgcaaa tcctgagact      660
catcaaacct atgaaagacg gtacaagta tactggaatc cgatctctga aacttgacat      720
gaacccaggc actggtattt ggcagagcat tgatgtgaag acagtgttgc aaaattggct      780
caaacaacct gaatccaact taggcattga aataaaagct ttagatgaga atggtcatga      840
tcttgctgta accttcccag gaccaggaga agatgggctg aatccgtttt tagaggtcaa      900
ggtaacagac acaccaaaaa gatccagaag ggattttggt cttgactgtg atgagcactc      960
aacagaatca cgatgctgtc gttaccctct aactgtggat tttgaagctt ttggatggga     1020
ttggattatc gctcctaaaa gatataaggc caattactgc tctggagagt gtgaatttgt     1080 attttttacaa aaatatcctc atactcatct ggtacaccaa gcaaacccca gaggttcagc    1140
aggcccttgc tgtactccca caaagatgtc tccaattaat atgctatatt ttaatggcaa     1200
agaacaaata atatatggga aaattccagc gatggtagta gaccgctgtg ggtgctcatg     1260
agatttatat taagcgttca taacttccta aaacatggaa ggttttcccc tcaacaattt     1320
tgaagctgtg aaattaagta ccacaggcta taggcctaga gtatgctaca gtcacttaag     1380
cataagctac agtatgtaaa ctaaaagggg aatatatgc aatggttggc atttaaccat      1440
ccaaacaaat catacaagaa agttttatga tttccagagt ttttgagcta aaggagatc      1500 aaattacatt tatgttccta tatattacaa catcggcgag gaaatgaaag cgattctcct     1560
tgagttctga tgaattaaag gagtatgctt taaagtctat ttctttaaag ttttgtttaa     1620
tatttacaga aaaatccaca tacagtattg gtaaaatgca ggattgttat ataccatcat     1680
tcgaatcatc cttaaacact tgaatttata ttgtatggta gtatacttgg taagataaaa     1740
ttccacaaaa atagggatgg tgcagcatat gcaatttcca ttcctattat aattgacaca     1800
gtacattaac aatccatgcc aacggtgcta atacgatagg ctgaatgtct gaggctacca     1860
ggtttatcac ataaaaaaca ttcagtaaaa tagtaagttt ctcttttctt caggggcatt     1920
ttcctacacc tccaaatgag gaatggattt tctttaatgt aagaagaatc attttttctag    1980 aggttggctt tcaattctgt agcatacttg gagaaactgc attatcttaa aaggcagtca     2040
aatggtgttt gttttatca aaatgtcaaa ataacatact tggagaagta tgtaattttg      2100
tctttggaaa attacaacac tgcctttgca acactgcagt ttttatggta aaataataga     2160
aatgatcgac tctatcaata ttgtataaaa agactgaaac aatgcattta tataatatgt     2220
atacaatatt gttttgtaaa taagtgtctc ctttttatt tactttggta tattttttaca     2280 ctaaggacat ttcaaattaa gtactaaggc acaaagacat gtcatgcatc acagaaaagc     2340
aactacttat atttcagagc aaattagcag attaaatagt ggtcttaaaa ctccatatgt     2400
taatgattag atggttatat tacaatcatt ttatatttt ttacatgatt aacattcact      2460
tatggattca tgatggctgt ataaagtgaa tttgaaattt caatggttta ctgtcattgt     2520
gtttaaatct caacgttcca ttattttaat acttgcaaaa acattactaa gtataccaaa     2580
ataattgact ctattatctg aaatgaagaa taaactgatg ctatctcaac aataactgtt     2640
```

```
acttttattt tataatttga taatgaatat atttctgcat ttatttactt ctgttttgta    2700
aattgggatt ttgttaatca aatttattgt actatgacta aatgaaatta tttcttacat    2760
ctaatttgta gaaacagtat aagttatatt aaagtgtttt cacatttttt tgaaagacaa    2820
aaa                                                                  2823
```

```
<210> SEQ ID NO 7
<211> LENGTH: 12
<212> TYPE: PRT
<213> ORGANISM: Artificial Sequence
<220> FEATURE:
<223> OTHER INFORMATION: synthetic transport protein

<400> SEQUENCE: 7

Arg Arg Arg Arg Arg Arg Arg Arg Arg Phe Phe Cys
1               5                   10

<210> SEQ ID NO 8
<211> LENGTH: 12
<212> TYPE: PRT
<213> ORGANISM: Artificial Sequence
<220> FEATURE:
<223> OTHER INFORMATION: synthetic transport protein

<400> SEQUENCE: 8

Arg Arg Arg Arg Arg Phe Phe Arg Arg Arg Arg Cys
1               5                   10

<210> SEQ ID NO 9
<211> LENGTH: 12
<212> TYPE: PRT
<213> ORGANISM: Artificial Sequence
<220> FEATURE:
<223> OTHER INFORMATION: synthetic transport protein
<220> FEATURE:
<221> NAME/KEY: misc_feature
<222> LOCATION: 2, 5, 8, 11
<223> OTHER INFORMATION: Xaa is 6-aminohexanoic acid

<400> SEQUENCE: 9

Arg Xaa Arg Arg Xaa Arg Arg Xaa Arg Arg Xaa Arg
1               5                   10

<210> SEQ ID NO 10
<211> LENGTH: 52
<212> TYPE: DNA
<213> ORGANISM: Homo sapiens

<400> SEQUENCE: 10
gaaaaaagat tatattgatt ttaaaatcat gcaaaaactg caactctgtg tt            52

<210> SEQ ID NO 11
<211> LENGTH: 50
<212> TYPE: DNA
<213> ORGANISM: Homo sapiens

<400> SEQUENCE: 11
acaatcatta ccatgcctac agagtgtaag tagtcctatt agtgtatatc                50

<210> SEQ ID NO 12
<211> LENGTH: 50
<212> TYPE: DNA
<213> ORGANISM: Homo sapiens

<400> SEQUENCE: 12
```

```
cttttcttttt cttattcatt tatagctgat tttctaatgc aagtggatgg         50
```

<210> SEQ ID NO 13
<211> LENGTH: 50
<212> TYPE: DNA
<213> ORGANISM: Homo sapiens

<400> SEQUENCE: 13

```
cccaggacca ggagaagatg ggctggtaag tgataactga aaataacatt         50
```

<210> SEQ ID NO 14
<211> LENGTH: 50
<212> TYPE: DNA
<213> ORGANISM: Homo sapiens

<400> SEQUENCE: 14

```
tgattgttct ttccttttca aacagaatcc gtttttagag gtcaaggtaa         50
```